US008107605B2

(12) United States Patent
Jaffres et al.

(10) Patent No.: US 8,107,605 B2
(45) Date of Patent: Jan. 31, 2012

(54) MEMORY AID FOR PERSONS HAVING MEMORY LOSS

(75) Inventors: Remy Jaffres, Le Bignon (FR); Gonzague de Raulin, Vannes (FR)

(73) Assignee: Hill-Rom SAS, Pluvigner (FR)

( * ) Notice: Subject to any disclaimer, the term of this patent is extended or adjusted under 35 U.S.C. 154(b) by 800 days.

(21) Appl. No.: 12/235,028

(22) Filed: Sep. 22, 2008

(65) Prior Publication Data
US 2009/0102913 A1    Apr. 23, 2009

Related U.S. Application Data

(60) Provisional application No. 60/975,388, filed on Sep. 26, 2007.

(51) Int. Cl.
*H04M 11/00* (2006.01)
(52) U.S. Cl. .................... 379/100.02; 709/217
(58) Field of Classification Search ............ 379/93.01, 379/100.02, 100.05; 709/217, 204; 348/14.01–14.08, 61, 207.99, E7.077, E5.024; 235/91 E
See application file for complete search history.

(56) References Cited

U.S. PATENT DOCUMENTS

| | | | |
|---|---|---|---|
| 5,208,745 A * | 5/1993 | Quentin et al. ................. | 700/83 |
| 5,283,819 A * | 2/1994 | Glick et al. ................ | 379/93.01 |
| 5,444,673 A | 8/1995 | Mathurin | |
| 5,717,430 A * | 2/1998 | Copland et al. .............. | 345/168 |
| 6,513,046 B1 | 1/2003 | Abbott, III et al. | |
| 6,549,915 B2 | 4/2003 | Abbott, III et al. | |
| 6,773,344 B1 | 8/2004 | Gabai et al. | |
| 6,842,877 B2 | 1/2005 | Robarts et al. | |
| 6,950,026 B2 | 9/2005 | Yamashita et al. | |
| 7,010,624 B1 * | 3/2006 | Zhou et al. ........................ | 710/8 |
| 7,155,456 B2 | 12/2006 | Abbott, III et al. | |
| 2001/0040986 A1 | 11/2001 | Farringdon et al. | |

(Continued)

FOREIGN PATENT DOCUMENTS

DE   203 09 332 U1   12/2004

(Continued)

OTHER PUBLICATIONS

European Search Report on European Patent Application No. EP 08253119.5, dated Jan. 29, 2009 (4 pages).

*Primary Examiner* — Curtis Kuntz
*Assistant Examiner* — Maria El-Zoobi
(74) *Attorney, Agent, or Firm* — Barnes & Thornburg LLP

(57) ABSTRACT

A simplified computer device is provided and may be used by persons having memory loss to connect via a network, such as the Internet, to one or more other computer devices. The simplified computer device is operable to obtain image, text and/or audio files from the other computer device for displaying on a display screen or for playing on an audio player, as the case may be, of the simplified computer devices to assist the persons with memory loss in recalling the identity and/or other information about their family members, friends, caregivers, and other acquaintances. Using a limited set of buttons on the simplified computer devices, the persons having memory loss can automatically link to one or more predetermined other computer devices and retrieve the image files and associated text and audio files. A local input module is coupleable to the simplified computer device and is usable for entry of images, text, and/or audio directly into the memory of the associated simplified computer devices for storage therein and/or for transmission to other devices of the network.

25 Claims, 2 Drawing Sheets

U.S. PATENT DOCUMENTS

| | | |
|---|---|---|
| 2002/0032689 A1 | 3/2002 | Abbott, III et al. |
| 2002/0083025 A1 | 6/2002 | Robarts et al. |
| 2003/0067555 A1 | 4/2003 | Han |
| 2003/0154476 A1 | 8/2003 | Abbott, III et al. |
| 2003/0217148 A1* | 11/2003 | Mullen et al. ............ 709/225 |
| 2004/0010325 A1* | 1/2004 | Naitoh .................... 700/65 |
| 2004/0160325 A1 | 8/2004 | Yamashita et al. |
| 2004/0246106 A1 | 12/2004 | Kain |
| 2006/0004680 A1 | 1/2006 | Robarts et al. |
| 2006/0073452 A1 | 4/2006 | Goldman et al. |
| 2006/0092445 A1 | 5/2006 | Muramatsu |
| 2007/0043459 A1 | 2/2007 | Abbott, III et al. |
| 2007/0061694 A1 | 3/2007 | Nortrup et al. |
| 2007/0083911 A1* | 4/2007 | Madden et al. ............ 725/135 |
| 2007/0174765 A1 | 7/2007 | Schleppenbach et al. |
| 2007/0189737 A1* | 8/2007 | Chaudhri et al. ........... 386/125 |
| 2007/0222772 A1 | 9/2007 | Amick |
| 2008/0027033 A1 | 1/2008 | Gonda et al. |
| 2008/0138783 A1 | 6/2008 | Karkanias et al. |

FOREIGN PATENT DOCUMENTS

| | | |
|---|---|---|
| GB | 2 299 878 A | 10/1996 |
| WO | WO 01/69830 A2 | 9/2001 |
| WO | WO 01/69830 A3 | 9/2001 |
| WO | WO 03/067555 A1 | 8/2003 |
| WO | WO 2008/027033 A1 | 3/2008 |

* cited by examiner

MEMORY AID FOR PERSONS HAVING MEMORY LOSS

This application claims the benefit, under 35 U.S.C. §119 (e), of U.S. Provisional Patent Application Ser. No. 60/975,388 which was filed Sep. 26, 2008 and which is hereby expressly incorporated by reference herein.

BACKGROUND

The present disclosure relates to a memory aid for persons having memory loss, such as persons having Alzheimer's disease. More particularly, the present disclosure relates to a simplified computer device with a video screen and audio player that is connectible to a network to retrieve files from remote locations.

Persons having memory loss, such as Alzheimer's disease, sometimes have difficulty recognizing or remembering other family members, friends, caregivers, other medical staff, and other acquaintances with whom such persons come into contact. This situation can be frustrating for the persons having memory loss and for the family members, friends, etc. Also, as older members of a family pass on, their memory of prior family members in the lineage or genealogy may be lost if not passed on to younger members of the family. Many stories and anecdotes about each of the ancestors in a person's family may also become lost if not passed on to younger members of the family.

SUMMARY

The present invention comprises an apparatus, a method of making an apparatus, a method of using an apparatus, and/or a system and associated methods having one or more of the features recited in the appended claims and/or the following features which, alone or in any combination, may comprise patentable subject matter:

An apparatus to aid the memory of persons experiencing memory loss may be provided. The apparatus may comprise a simplified computer device having a first housing, a display screen carried by the first housing, an audio player carried by the first housing, and control circuitry carried by the first housing. The control circuitry may be operable to control images displayed on the display screen and to control audio messages played by the audio player. The control circuitry may be configured to establish a communication link with at least one other predetermined communication site on a network during operation of the apparatus. The control circuitry may be operable to initiate retrieval of remote image files, remote text files, and remote audio files from the predetermined communication site.

The simplified computer device may further have a telephone handset coupled to the control circuitry. The telephone handset may be movable relative to the first housing and operable to place and receive telephone calls. The telephone handset may be coupled to the control circuitry of the simplified computer device via a wireless communication link or via a telephone cord that extends between the telephone handset and the first housing.

The apparatus may further comprise a local input module that is coupleable to the control circuitry of the simplified computer device. The local input module may have a second housing and a scanner that is carried by the second housing and that is operable to scan images of photos or other documents fed through the scanner to create local image files. The local input module may comprise a microphone that is carried by the second housing and that is operable to receive verbal statements to create local audio files to be associated with the local image files. The microphone may be situated on a gooseneck or other type of microphone stand that extends upwardly from the second housing or the microphone may be located within the housing which may have one or more slots or openings to permit sound to reach the microphone with less attenuation than if such slots or opening were not provided. The local input module may also have a keyboard that is carried by the second housing and that is usable to type text messages to be associated with the local image files.

During display of one of the local image files on the display screen, the audio player may automatically play at least one of the local audio files that is associated with the local image file being displayed. The audio player may send a signal to the handset resulting in the local audio file being output as an audible audio message by a speaker of the telephone handset. During display of the each local image file on the display screen, at least one of the local text files that is associated with the local image being displayed may also be displayed on the display screen. The local text file being displayed may be displayed on a first portion of the display screen and the local image file being displayed may be displayed on a second portion of the display screen, such as in a split screen format. The local text file being displayed may be superimposed on a portion of the local image file being displayed.

During display of one of the remote image files on the display screen, the audio player may automatically play at least one of the remote audio files that is associated with the remote image file being displayed. It should be noted that the use of the adjectives "local" and "remote" in the summary, the description, and in the claims is intended to simply distinguish between the files that were accessed locally by the simplified computer device from the local input module and the files that were accessed by the simplified computer device from one or more computer devices situated at a remote location such as, for example, the preprogrammed communication site or in another room of the same building or from a website or from the home of a family member and so on.

The audio player may send a signal to the handset resulting in the remote audio file being output as an audible audio message by a speaker of the telephone handset. During display of the one remote image file on the display screen, at least one of the remote text files that is associated with the remote image file being displayed may also be displayed on the display screen. The remote text file being displayed may be displayed on a first portion of the display screen and the remote image file being displayed may be displayed on a second portion of the display screen, such as in a split screen format. The remote text file being displayed may be superimposed on a portion of the remote image file being displayed.

The local image files, the local audio files and the local text files created by the local input module may be stored in memory of the control circuitry of the simplified computer device. During communication of the simplified computer device via the communication link with the communication site, the local image files, the local audio files, and the local text files stored in memory of the control circuitry of the simplified computer device may be transmitted to the communication site for storage at the communication site. The communication site may comprise a website that facilitates transmission of the remote image files, the remote audio files, and the remote text files between a user of the simplified computer device and a computer device operated by one of a family member, a friend, a caregiver, and an acquaintance of the user. The communication site may comprise a computer device operated by one of a family member, a friend, a caregiver, and an acquaintance of the user. The communication link may comprise the Internet, an Ethernet, an intranet, or other type of network such, for example, a local area network or a wide area network.

The apparatus may further comprise a camera that may be coupled to the control circuitry of the simplified computer device. The camera may be operable to capture images in substantially real time for transmission to a remote computer device. The operation of the camera coupled to the simplified computer device may be controlled by signals sent from a remote computer device. The operation of the camera coupled to the simplified computer device may be controlled by signals sent from the communication site.

The local input module may couple to the simplified computer device in side-by-side relation such that an upper surface of the first housing cooperates with an upper surface of the second housing to form a substantially contiguous upper surface. When the local input module is coupled to the simplified computer device, a front surface of the first housing may cooperate with a front surface of the second housing to form a substantially contiguous front surface and a rear surface of the first housing cooperates with a rear surface of the second housing to form a substantially contiguous rear surface. The coupling of the local input module to the simplified computer device may be provided by a first electrical coupler of the local input module mating with a second electrical coupler of the simplified computer device. Additional mechanical couplers may be provided optionally to enhance the robustness of the coupling.

The upper surface of the first housing may have an opening in which the display screen is located or through which the display screen is viewable. The upper surface of the second housing may have one or more openings in which keys of the keyboard are located or through which keys of the keyboard are accessible. In such an arrangement, the keyboard of the local input module is beside the display screen and generally along the same plane. The keys of the keyboard may be push button keys or may be membrane switch keys, or may even be combinations of these. The keyboard may comprise a touch screen. The keyboard may comprises letter keys, each letter key being designated for one letter of the alphabet, and/or number keys, each number key being designated for one of the numbers 0-9, and/or additional keys, such as functions keys (e.g., F1, F2, F3, etc. or "Delete," "Tab," "Enter," "Page Up," "Page Down," "Ctrl," etc.) or such as arithmetic operator keys (e.g., "+," "-," "=," and so on) or such as arrow keys (e.g., up arrow, down arrow, left arrow, and/or right arrow).

It is contemplated that, in some embodiments, the user inputs, such as control buttons, of the simplified computer device are lesser in number and complexity than those found on a typical computer keyboard, and are more on the order of the number and complexity of keys found on a typical telephone key pad. For persons having memory loss, the simplified computer device may have keys that are lesser in number and complexity than the keys of a typical telephone key pad.

An apparatus for displaying images and playing audio recordings, therefore, may comprise a housing, control circuitry carried by the housing, and a video screen carried by the housing, coupled to the control circuitry, and operable to display an image. The apparatus may further have an audio player carried by the housing, coupled to the control circuitry, and operable to play an audio recording. The apparatus may also have a telephone handset coupled to the control circuitry. The telephone handset may be movable relative to the first housing and operable to place and receive telephone calls. The telephone handset may have user inputs that are usable to place phone calls. The control circuitry may be configured to link to a preprogrammed website without use of any alphanumeric keyboard and without use of any of the user inputs of the handset.

The apparatus may have a first user input member that is coupled to the housing and that is used to initiate the linking of the control circuitry to the preprogrammed website. After the control circuitry is linked to the preprogrammed website, data files may be transmitted to the control circuitry from the preprogrammed website. Each of the data files may comprise an image file and an associated audio file. The control circuitry may operate to display the image file of a first data file on the display screen and, during the display of the image file on the display screen, the control circuitry may operate automatically to play the audio file using the audio player.

The apparatus may have a second user input member that is coupled to the housing and that is used to initiate the audio player playing a first audio file during display of an associated first image file on the display screen. The apparatus also may have a third user input member that is coupled to the housing and that is used to command the control circuitry to display a second image on the display screen. Thus, the third user input member may be used to scroll through the image files and the second user input may be used to initiate playing the audio file associated with the image file being displayed at any given time. The first user input may serve as an on/off user input member such that, when the apparatus is turned on by a user, the control circuitry may automatically link to the preprogrammed website and such that, when the apparatus is turned off by a user, the control circuitry may automatically disconnect from the preprogrammed website.

The first, second, and third user input members may be the only user input members coupled to housing. The telephone handset may include a speaker and, when the audio player carried by the housing plays an audio recording, the sound may emanate from the speaker. The telephone handset may include a volume control to control the volume of the sound emanating from the speaker.

Systems having any of the above-described apparatuses in combination with other computer devices, for example, to form a local area network (LAN), a wide area network (WAN), an Ethernet within a building, or an intranet among several geographic locations of a corporation, for example, are contemplated. Also contemplated are methods of using and methods of making the above-described apparatuses and method. It is also contemplated that the above-described apparatus may be integrated into other devices such as, for example, patient care beds, chairs, and desks. Methods of making and using such integrated devices are contemplated.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures, in which.

DETAILED DESCRIPTION OF ILLUSTRATIVE EMBODIMENTS

Figure 1:
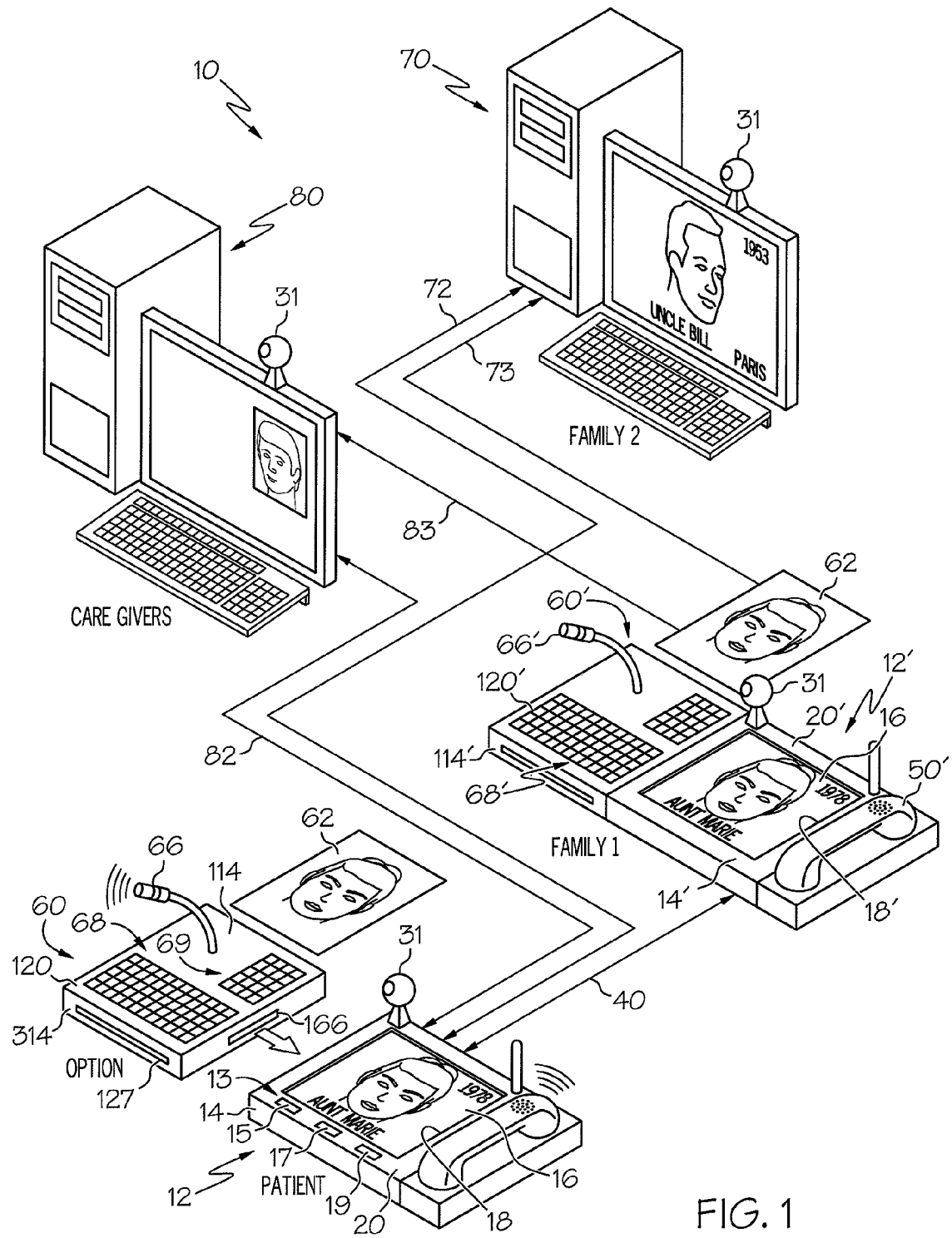
FIG. 1 is a diagrammatic view of a system having a pair of simplified computer devices which may be used by persons having memory loss to connect via a network to two computer devices, the simplified computer devices being operable to obtain image, text and/or audio files which are displayed on a display screen or played on an audio player, as the case may be, of the simplified computer devices to assist the persons with memory loss in recalling the identity and/or other information about other family members, friends, caregivers, and other acquaintances, the simplified computer devices having a housing that caries the display screen and the audio player, the simplified computer devices also having a telephone handset and a camera coupled thereto, and the system further including local input modules that are coupleable to respective simplified computer devices for entry of images, text, and/or audio directly into the memory of the associated simplified computer devices for storage of the files therein and/or for transmission of the files to other devices of the network.

A system 10 comprises one or more simplified computer devices 12 which are designed for use by persons experiencing memory loss, such as persons having Alzheimer's disease. Many persons experiencing memory loss are elderly persons who may not be accustomed to operating sophisticated electronic devices, such as personal computers. However, such persons are likely accustomed to operating simpler devices such as telephones. Thus, simplified computer devices 12 are designed to have simplified user inputs 13, as shown diagrammatically in FIG. 2, which are no more complex to understand and to operate than the typical user inputs of a telephone.

The primary functions of device 12 are to display images of pictures and to play a sound recording that describes the image. The images and the sound recordings may originate from a variety of sources, such as from other devices 12', as indicated diagrammatically by doubled headed arrow 40 in FIG. 1; from a local input module 60 which is directly coupleable to and decoupleable from device 12; from a personal computer 70 of a family member, as indicated diagrammatically by double headed arrow 72 in FIG. 1; from a work computer 80 of a caregiver, as indicated diagrammatically by double headed arrow 82 in FIG. 1; or from a computer, such as a server, associated with a website. Each of devices 12' and computers 70, 80 is considered a communication site according to this disclosure, as is a server computer associated with a website and as are any other computer devices with which device 12 may communicate electronically to transfer data. In the illustrative example, device 12' and/or its associated local input module 60' may communicate electronically to upload images and sound recordings to computers 70, 80 as indicated diagrammatically in FIG. 1 by double headed arrows 73, 83, respectively.

Optionally, a text message may also be displayed with the image, either in a split screen format or superimposed over a portion of the image. Because a person's memory has been found to be enhanced when the person is exposed to information via multiple ones of the person's senses, by having a person see an image, hear a sound recording about the image, and in some instances read a text message about the image substantially at the same time, device 12 is designed to permit the image, the sound recording and the text message to be presented to the user at the same time. According to this disclosure, images are said to be stored as image files, sound or audio recordings are said to be stored as audio files, and text messages are said to be stored as text files. It should be appreciated, therefore, that a particular image file, a particular audio file, and/or a particular text file may be associated with each other and stored together as associated data files or merged together into a data file that is later parsed into the respective image file, audio file, and text file for processing and display or playing.

Figure 2:
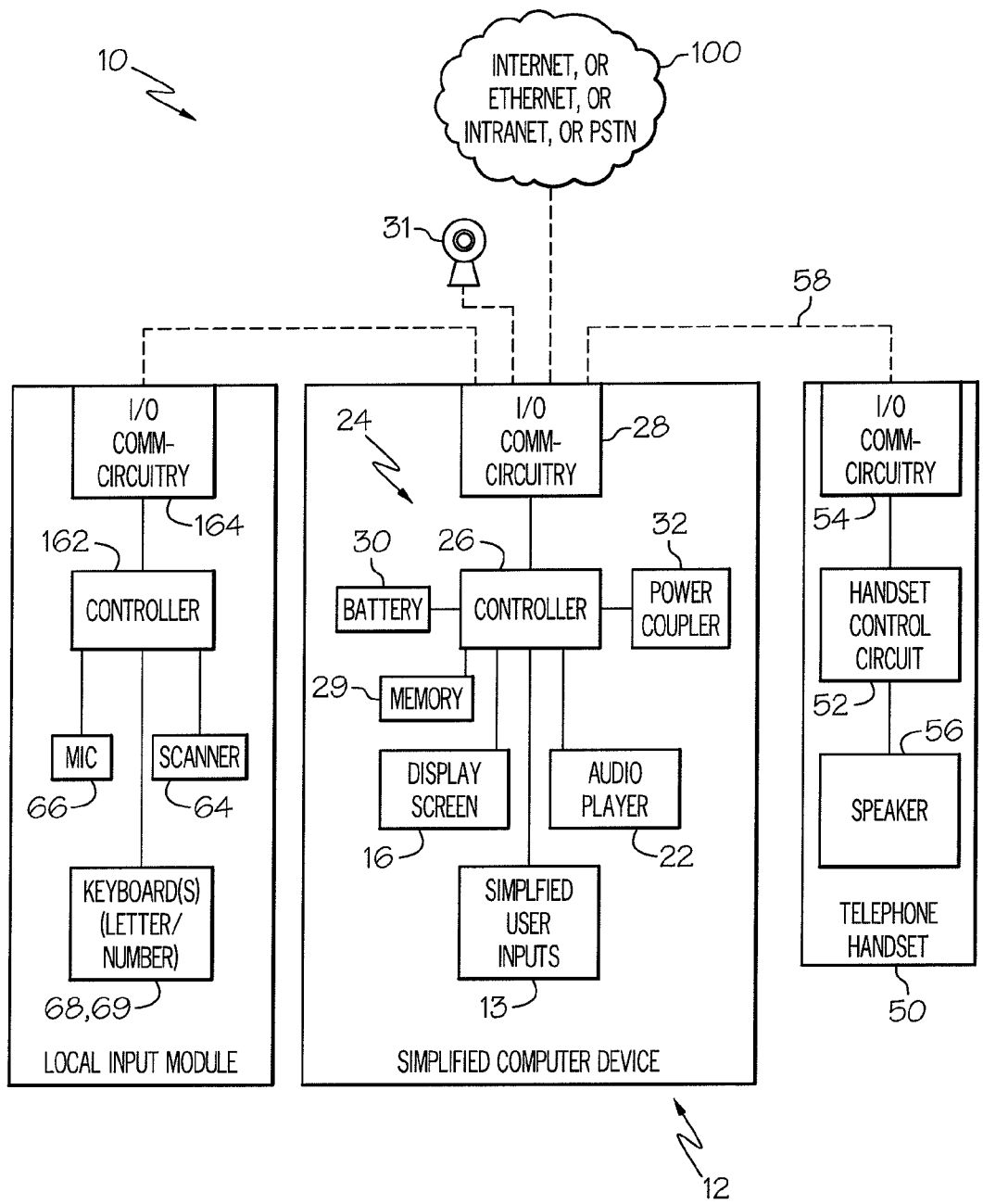
FIG. 2 is a block diagram showing the various high level circuitry components of the simplified computer device, the local input module, and telephone handset.

In the illustrative example, devices 12, 12' have telephone handsets 50, 50', respectively, which operate as a standard telephone. Accordingly, each handset 50, 50' has a standard telephone keypad which is not shown but which is well-known to anyone who has ever used a telephone. In other embodiments, handsets 50, 50' are omitted. The double headed arrows 40, 72, 82, 73, 83 in FIG. 1 are intended to represent some of the communication links in system 10. Devices 12, 12' and computer 70, 80 may be arranged as a local area network (LAN), a wide area network (WAN), an Ethernet within a building such as in a nursing home, or an intranet such as that established between computer devices located at a caregiver's office, a family member's home, and the home of a person experiencing memory loss. Furthermore, devices 12, 12' and computers 70, 80 may communicate with each other via the Internet. In addition, telephone handset 50 may be used to call any other regular telephone or telephone handset 50' of device 12'. Using Voice over Internet Protocol (VoIP), handset 50 may be used to place calls to computers 70, 80, for example. In FIG. 2, the various communication arrangements and links, including the Internet and a public switched telephone network (PSTN), is illustrated diagrammatically as cloud 100.

In the illustrative example, each of devices 12, 12' and computers 70, 80 have a camera 31 but that need not be the case. Thus, when devices 12, 12' and computers 70, 80 having cameras 31 are used as telephonic communication devices, cameras 31 at the caller and recipient locations capture images of the caller and recipient, in substantially real time, and such images are displayed on the respective display screens of devices 12, 12' and computers 70, 80 as the case may be.

Device 12 is programmed to establish a communication link with one or more predetermined communication sites and to initiate retrieval of the image, audio, and/or text files that are stored in the computer devices, such as illustrative device 12' and computers 70, 80, associated with the communication site(s) for displaying and playing on device 12. For example, in some embodiments, device 12 is programmed to link to a particular web address identified by a universal resource locator (URL) which is associated with a server of a website that facilities subsequent linking to device 12' and computers 70, 80. In LAN, WAN, Ethernet, and intranet embodiments, device 12 is programmed with the network addresses of the devices from which device 12 is to receive data files according to the protocols of the particular LAN, WAN, Ethernet, or intranet in which device 12 is included. Device 12 then operates in a systematic programmed manner to retrieve the data files from the communication site(s), display the various image and text files and to play the various audio files to assist the user in remembering the people and/or events and/or places, etc. depicted by the image files and described by the text and audio files. In some embodiments, device 12 automatically downloads multiple data files in response to the communication link being established and, in other embodiments, device 12 download data files one-at-a-time as a user retrieves them with device 12.

In the illustrative example of FIG. 1, the simplified user inputs 13 comprise a first user input member 15, a second user input member 17, and a third user input member 19. Members 15, 17, 19 are buttons in the illustrative embodiment but may be levers, switches (such as membrane switches, toggle switches or the like), touch sensors (including portions of a touch screen), or the like in other embodiments at the discretion of the device designer. First user input member 15 is used to initiate the linking of device 12 to the preprogrammed communication site(s). After the device 12 is linked to the preprogrammed communication site(s), data files are then transmitted to device 12. Second user input member 17 is used to initiate playing of the audio file that is associated with the image file that is being displayed currently on device 12. Third user input member 19 is used to command the device 12 to display another image. Thus, in this illustrative example, the third user input member 19 is used to scroll through the image files and the second user input 17 is used to initiate playing the audio file associated with the image file being displayed at any given time. Also in the illustrative example, first user input 19 serves as an on/off user input member such that, when device 12 is turned on by a user, device 12 automatically links to the preprogrammed communication site(s), as already mentioned, and such that, when device 12 is turned off by a user, device 12 automatically disconnects from the communication site(s).

In the illustrative example, the first, second, and third user input members are the only user input members of device 12, other than the telephone keypad of handset 50 if such a handset 50 is provided. In other embodiments, additional user input members such as a volume control button or knob, for example, may be provided on device 12 for the user to control other aspects of the operation of device 12 concerning the retrieval, display, and playing of image, audio, and text files. However, it is contemplated that the number and complexity of the simplified user inputs 13 of device 12, even if further inputs in addition to three inputs members 15, 17, 19 just described, will be approximately equal to or lesser than the number of keys and/or buttons on the key pad of handset 50.

As mentioned above, local input modules 60, 60' are provided for coupling directly to devices 12, 12', respectively. Module 60' is substantially similar to module 60 and so the description that follows refers only to module 60. The primary functions of module 60 are to permit creation of image files by scanning photographs 62 using a scanner 64, to permit recording of audio files using a microphone 66, and to permit creation of text files using a letter keyboard 68 and/or a number keyboard 69. With regard to device 12, which is used by the person experiencing memory loss, it is contemplated that module 60 will be connected only temporarily to device 12, perhaps by a family member or caregiver visiting the person, for creation of associated image, audio, and text files for transmission directly to and storage in device 12. Of course, if the person experiencing memory loss is capable of using module 60, then that person can operate module 60 as well. However, in most instances, when the person experiencing memory loss uses device 12, it is contemplated that the associated module 60 will not be attached to device 12. Of course, this need not be the case in those instances when the person is experiencing only very limited memory loss and/or is otherwise capable of operating module 60 himself or herself and is also able to operate device 12 even if module 60 is attached. On the other hand, it is contemplated that if a family member, friend, or other acquaintance is operating device 12', the associated module 60' is attached and is, in fact, used to control the operation of device 12'. As such, device 12' in the illustrative example does not have input members 15, 17, 19 because they are not needed due to the fact that the user of device 12' will control its use with module 60'.

The description below of device 12 is equally applicable to device 12' unless otherwise noted, as was the case above in which device 12 was described as having input members 15, 17, 19 and device 12' was described as lacking such input members. Like portions of devices 12, 12' are denoted with the same reference numbers, but the prime symbol is used with the reference numbers associated with device 12'.

Device 12 has a housing 14 with a display screen 16 that is situated within, or viewable through, an opening 18 provided in an upper surface or wall 20 of the respective housing 14 as shown in FIG. 1. Device 12 also has an audio player 22 as shown diagrammatically in FIG. 2. Device 12 has control circuitry 24 coupled to the display screen 14 and to the audio player 22. The control circuitry 24 includes a controller 26, input/output (I/O) communication circuitry 28, memory 29, and any other circuitry that cooperates with controller 26 and circuitry 28 to control the operation of device 12. Control circuitry 24 may include, for example, a display driver (not shown) and power control circuitry, such as circuitry for handling current and voltage levels provided to device 12 via a battery 30 or power coupler 32 and processing circuitry, for example. Power coupler 32 may comprise a standard AC power plug and cord in some embodiments. Device 12 may receive power over its Internet or Ethernet connection and feed this power to handset 50 and/or module 60 in some embodiments. Controller 26 is coupled electrically to user inputs 13, display screen 16, audio player 22, circuitry 28, memory 29, battery 30, and coupler 32 as shown diagrammatically in FIG. 2.

Handset 50 includes handset control circuitry 52, I/O communication circuitry 54, and a speaker 56. The I/O communication circuitry 52 couples to the I/O communication circuitry 28 of device 12 via a wireless coupling, such that handset 50 is considered a "wireless" handset, or via a wired coupling such as a telephone cord, as indicated diagrammatically by dashed line 58 in FIG. 2. Circuitry 52 is intended to represent all of the circuitry of the handset, including the telephone keypad, and the microphone and ear phone of the handset 50. Circuitry 52 is electrically coupled to the I/O circuitry 52 and to speaker 56. Speaker 56 enables handset 50 to have a speaker phone capability. In addition, when the audio player 22 of device 12 plays an audio file, the sound may emanate from speaker 56 of handset 50 in some embodiments. Accordingly, handset 50 may have volume control to adjust the volume level at which the audio files are played. In other embodiments, device 12 may have its own speaker and/or volume control.

Module 60 includes a controller 162 and I/O communication circuitry 164 as shown diagrammatically in FIG. 2. Scanner 64, microphone 66, keyboards 68, 69, and circuitry 162 are coupled electrically to controller 162. The image data used to make up the image files by scanning photographs 62, for example, through scanner 64 is transmitted via controller 162 and I/O communication circuitry 164 of module 60 to memory 29 of device 12 via I/O communication circuitry 28 and controller 26 of device 12. The connection between circuitry 164 of module 60 and circuitry 28 of device 12 is made due to a direct connection between first and second electrical connectors 166 of device 12 and module 60. One of connectors 166 can be seen in FIG. 1 with respect to module 60. Similar data transfer between module 60 and device 12 occurs with regard to the voice data captured by microphone 66 used to make up the associated audio files and the key presses of the keys of keyboards 68, 69 which are used to make up the associated text files.

It is contemplated that controllers 26, 162 are microprocessor-based or microcontroller-based controllers, and so too may be handset control circuitry 52 in some embodiments. Any number of microprocessors or microcontrollers available from companies such as Intel Corporation, Texas Instruments, Inc., Motorola Corporation, and others are suitable for use in device 12 and module 60. In other embodiments, controller 26 may be the primary controller of all the functionality of device 12, module 60, and handset 50, such that only controller 26 need be a microprocessor-based or microcontroller-based controller.

In the illustrative example, input members 15, 17, 19 extend upwardly through, or are accessible within or through, associated openings in upper surface 20 of housing 14 as shown in FIG. 1. Similarly, the keys of keyboards 68, 69 of module 60 extend upwardly through, or are accessible within or through, an associated opening in an upper surface or wall 120 of a housing 114 of module 60. When module 60 is coupled to device 12, surfaces 20, 120 form a substantially contiguous upper surface 20, 120 such that display screen 16 is beside keyboards 68, 69 in substantially a common plane. In the illustrative example, microphone 66 is provided at the end of a flexible gooseneck stand 166, but it is within the scope of this disclosure for microphone to be within housing 114, in which case, additional slots may be provided in housing 114 to indicate the location of the microphone and to reduce the attenuation of the sound reaching the microphone. Also in the illustrative example, a front surface 214 of housing 14 and a front surface 314 of housing 114 cooperate to form a contiguous front surface 214, 314 when module 60 is coupled to device 12. The same type of contiguous surface is provided by the rear surfaces of module 60 and device 12 when module 60 is coupled to device 12. The distance between the front and rear wall of each of module 60 and device 12 is approximately the same at the longitudinal length of handset 50 as shown in FIG. 1. In the illustrative example, a slot 127 is provided in the front wall 314 of module 60 to provide an exit opening for photographs 62 to exit after being scanned by scanner 64 of module 60. A similar slot is provided in the rear wall of module to provide an entrance opening for photographs to be scanned. When module 60 is coupled to device 12, the sidewalls having couplers 166 either abut or are in closely confronting relation with a minimal amount of clearance therebetween when module 60 is coupled to device 12.

While it is contemplated that photographs will be fed through scanner 64, it would be possible to scan other types of documents, such as magazine pages, drawings, marriage certificates, and the like. Furthermore, digital photos may be downloaded as image files to device 12 from computer devices 70, 80 or device 12' and stored therein. Audio files and/or text files may be created and associated with such digital photos using module 60 or module 60'.

Although certain illustrative embodiments have been described in detail above, variations and modifications exist within the scope and spirit of this disclosure as described and as defined in the following claims.

The invention claimed is:

1. An apparatus to aid the memory of persons experiencing memory loss, the apparatus comprising
a simplified computer device having a first housing, a display screen carried by the first housing, an audio player carried by the first housing, and control circuitry carried by the first housing, the control circuitry being operable to control images displayed on the display screen and to control audio messages played by the audio player, the control circuitry being configured to establish a communication link with at least one other predetermined communication site on a network during operation of the apparatus, the control circuitry being operable to initiate retrieval of remote image files, remote text files, and remote audio files from the predetermined communication site, the simplified computer device further having a telephone handset coupled to the control circuitry, the telephone handset being movable relative to the first housing and operable to place and receive telephone calls, and
a local input module coupleable to the control circuitry of the simplified computer device, the local input module having a second housing, a scanner carried by the second housing and operable to scan images of photos fed through the scanner to create local image files, a microphone carried by the second housing and operable to receive verbal statements to create local audio files to be associated with the local image files, and a keyboard carried by the second housing and usable to type text messages to be associated with the local image files.

2. The apparatus of claim 1, wherein the simplified computer device is configured so that, during display of one of the local image files on the display screen, the audio player automatically plays one of the local audio files that is associated with the local image file being displayed.

3. The apparatus of claim 2, wherein the audio player is configured to send a signal to the handset resulting in the local audio file being output as an audible audio message by a speaker of the telephone handset.

4. The apparatus of claim 2, wherein the simplified computer device is configured so that, during display of the one local image file on the display screen, one of the local text files that is associated with the local image being displayed is also displayed on the display screen.

5. The apparatus of claim 4, wherein the local text file being displayed is displayed on a first portion of the display screen and the local image file being displayed is displayed on a second portion of the display screen.

6. The apparatus of claim 4, wherein the local text file being displayed is superimposed on a portion of the local image file being displayed.

7. The apparatus of claim 1, wherein the simplified computer device is configured so that, during display of one of the remote image files on the display screen, the audio player automatically plays one of the remote audio files that is associated with the remote image file being displayed.

8. The apparatus of claim 7, wherein the simplified computer device is configured so that the audio player sends a signal to the handset resulting in the remote audio file being output as an audible audio message by a speaker of the telephone handset.

9. The apparatus of claim 7, wherein the simplified computer device is configured so that, during display of the one remote image file on the display screen, one of the remote text files that is associated with the remote image file being displayed is also displayed on the display screen.

10. The apparatus of claim 9, wherein the remote text file being displayed is displayed on a first portion of the display screen and the remote image file being displayed is displayed on a second portion of the display screen.

11. The apparatus of claim 9, wherein the remote text file being displayed is superimposed on a portion of the remote image file being displayed.

12. The apparatus of claim 1, wherein the local image files, the local audio files and the local text files created by the local input module are stored in memory of the control circuitry of the simplified computer device.

13. The apparatus of claim 12, wherein the simplified computer device is configured so that, during communication of the simplified computer device via the communication link with the communication site, the local image files, the local audio files, and the local text files stored in memory of the control circuitry of the simplified computer device are transmitted to the communication site for storage at communication site.

14. The apparatus of claim 1, wherein the communication site comprises a website that facilitates transmission of the remote image files, the remote audio files, and the remote text files between a user of the simplified computer device and a computer device operated by one of a family member, a friend, a caregiver, and an acquaintance of the user.

15. The apparatus of claim 1, wherein the communication site comprises a computer device operated by one of a family member, a friend, a caregiver, and an acquaintance of the user.

16. The apparatus of claim 1, wherein the communication link comprises the Internet, an Ethernet, an intranet, a local area network, or a wide area network.

17. The apparatus of claim 1, further comprising a camera coupled to the control circuitry of the simplified computer device and operable to capture images in substantially real time for transmission to a remote computer device.

18. The apparatus of claim 17, wherein the operation of the camera coupled to the simplified computer device is controlled by signals sent from a remote computer device.

19. The apparatus of claim 17, wherein the operation of the camera coupled to the simplified computer device is controlled by signals sent from the communication site.

20. The apparatus of claim 1, wherein the local input module couples to the simplified computer device in side-by-side relation such an upper surface of the first housing cooperates with an upper surface of the second housing to form a substantially contiguous upper surface, a front surface of the first housing cooperates with a front surface of the second housing to form a substantially contiguous front surface, and a rear surface of the first housing cooperates with a rear surface of the second housing to form a substantially contiguous rear surface.

21. The apparatus of claim 20, wherein the upper surface of the first housing has an opening in which the display screen is located or through which the display screen is viewable and wherein the upper surface of the second housing has one or more openings in which keys of the keyboard are located or through which keys of the keyboard are accessible.

22. The apparatus of claim 1, wherein keys of the keyboard comprise push button keys or comprise membrane switch keys.

23. The apparatus of claim 1, wherein the telephone handset is coupled to the control circuitry of the simplified computer device via a wireless communication link.

24. The apparatus of claim 1, wherein the telephone handset is coupled to the control circuitry of the simplified computer device via a telephone cord that extends between the telephone handset and the first housing.

25. An apparatus to aid the memory of persons experiencing memory loss, the apparatus comprising a simplified computer device having a first housing, a display screen carried by the first housing, an audio player carried by the first housing, and control circuitry carried by the first housing, the control circuitry being operable to control images displayed on the display screen and to control audio messages played by the audio player, the control circuitry being configured to establish a communication link with at least one other predetermined communication site on a network during operation of the apparatus, the control circuitry being operable to initiate retrieval of remote image files, remote text files, and remote audio files from the predetermined communication site, and a local input module coupleable to the control circuitry of the simplified computer device, the local input module having a second housing, a scanner carried by the second housing and operable to scan images of photos fed through the scanner to create local image files, a microphone carried by the second housing and operable to receive verbal statements to create local audio files to be associated with the local image files, and a keyboard carried by the second housing and usable to type text messages to be associated with the local image files.

* * * * *